Aug. 30, 1966 D. WALKER ET AL Plant Pat. 2,666
GLADIOLUS PLANT
Filed Aug. 2, 1965
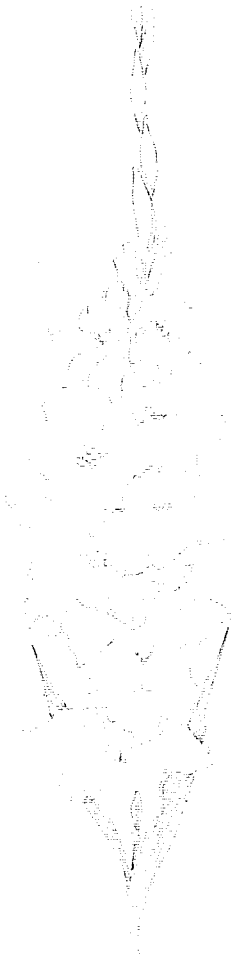
INVENTORS.
DON WALKER and
BY AUDREY WALKER
Burton L. Lilling
ATTORNEY United States Patent Office Plant Pat. 2,666

Patented August 30, 1966

2,666

GLADIOLUS PLANT

Don Walker and Audrey Walker, both of
323 Aquetong Road, New Hope, Pa.
Filed Aug. 2, 1965, Ser. No. 476,769
1 Claim. (Cl. Plt.—85)

Our new invention relates to a new and distinct variety of gladiolus plant.

The outstanding characteristic of our new gladiolus plant is its green color.

While it is true that gladiolus with a greenish hue are known, they are not satisfactory for use because of various faults, such as poor health, insufficient bud count, lack of opening ability after being shipped dry, and lack of modern ruffling. The instant variety provides a gladiolus plant with a true green color that does not suffer from any of the above disadvantages. It is rugged and vigorous in growth, is uniquely disease-resistant, has exceptional height and bud count, opens after shipping dry, produces green foliage with no chlorophyll deficiency, and is the only commercially useful green gladiolus in existence that is ruffled.

We have asexually reproduced the new variety by cormels through several generations in New Hope, Pennsylvania, and established that the characteristics and distinctions of the variety are true and are transmitted through succeeding propagations.

The new variety was obtained by crossing two gladiolus varieties, to wit, "Green Ice" and an unpatented, unnamed and unintroduced seedling by a cross of "Florence Nightingale" and "Aureole." The seedling was the seed parent and "Green Ice" the pollen parent. All of the above named varieties are unpatented.

The drawing shows a typical specimen of a flower spike of the new variety, with the flowers in varied stages of growth. Some are shown as closed buds, others are shown as partially opened buds, and others as fully opened buds. The colors depicted are as nearly true as is possible in this type of reproduction.

The following is a detailed description of the new variety.

The variety was first observed and grown in New Hope, Pennsylvania.

Succeeding generations have established that the distinguishing characteristics of the variety hold true through propagations by plantings derived from cormels.

*The plant*

*Growth habits.*—Vigorous and consistent. The blossom spike attains an average height of sixty inches under normal cultural conditions. The stem is slender, tall and graceful. It does not crook.

*Blooming habit.*—The blooming habit is early. Under normal conditions the first bloom appears approximately 75 days after planting.

*Stems.*—The stems are exceptionally tall and straight. Freedom from crooking is one of the features of this variety. The diameter of the stem just above the bulb is approximately one-half of an inch. The stems are approximately the same color as the leaves (Sheeles Green #860) or a shade lighter.

*Foliage.*—The corm of the new variety regularly produces at least seven leaves, and at times nine leaves from large bulbs. From the top of the corm to ground level the leaves surrounding the stem are colored shades of Rhodamine Purple (Plate #29 of the Horticultural Color Chart issued by the British Colour Council). Above ground they are colored a rich, deep green (Sheeles Green #860 in the Horticultural Color Chart issued by the British Colour Council). The leaves of this variety have no trace whatsoever of the chlorophyll deficiency characteristic of its pollen parent. The average leaf is one and one-half inches at the base, grows thirty six inches tall, and tapers gracefully to a point. The leaves are tall, slim and upright with a smooth edge. The parallel veins are slightly raised, giving the leaf a ribbed appearance. Sometimes small parts of the leaf are lightly crinkled.

*Disease resistance.*—The variety has been found to be unusually resistant to the usual gladiolus plant diseases of a bacterial, viral, or fungoid genesis as compared with other varieties grown therewith.

*Corms.*—The com of the new variety is one and three quarter inches in diameter, plump and relatively high-crowned. The paper-like husks are straw colored at the point of their attachment to the base of the corm, turning to progressive shades of Rhodamine Purple (Plate #29 of the Horticultural Color Chart issued by the British Colour Council) as they approach the base of the stem. The color of the flesh of the bulb is Straw Yellow (Plate #604 of the Horticultural Color Chart of the British Colour Council). The corm produces from twenty-five to fifty cormels, whose flesh is white and protected by a relatively soft beige outer skin. The size of the corm may vary somewhat depending upon the size of the stock from which the bulb was grown.

*The flower*

*Spike.*—The spike is tall and regularly carries 23 to 28 buds. The average flowerhead under normal conditions grows to at least thirty inches, which is unusually long.

*Bud.*—The average bud is about three to three and one-half inches in length when opening but smaller at the top. The length of the buds diminish naturally in size towards the tip of the flower spike. Before opening the buds are the deepest shade of Sap Green (Plate #62 of the Horticultural Chart issued by the British Colour Council) and reveal attractively ruffled edges. Three or four buds will open the first blooming day and two or three buds will open each day thereafter. The plant will hold eight to ten florets open in good condition before the lower ones break down. Above the open florets six buds will usually show in color.

*Flower.*—The flowerhead of the new variety has a formal placement wherein all florets face forward and there is no vertical separation between them. The individual florets average about five inches in dameter at the bottom of the flowerhead, and decrease in size progressively in perfect proportion approaching the tip. The florets are somewhat round, slightly recurved and quite ruffled. The flowers keep well.

*Petals.*—The petals are also somewhat round, slightly recurved and ruffled. The petals have slightly heavier than average substance. The upper petals are approximately two inches wide and the lower lip petals are approximately one and one-half inches wide. The flower has no fragrance. The petals of the variety, by reference to the Horticultural Color Charts issued by the British Colour Council, are Sap Green in the center blending through all the successively lighter shades of Sap Green (Plates 62/1 and 62/2) to the lightest of Sap Green (62/3) at the outer edge. The blend is even and pleasing.

*Reproductive organs*

*Stamens.*—The stamens are white and are marked underneath with two longitudinal stripes of Sea-Lavender Violet (Horticultural Color Chart of British Colour Council, Plate 637/2).

*Pistil.*—The pistil is pure white in color.

The new variety was obtained by crossing two gladiolus varieties, to wit, "Green Ice" and a cross of "Florence Nightingale" and "Aureole."

The parents of the new variety are registered with the North American Gladiolus Registry published in Sardinia, New York.

Having thus described our invention and illustrated its use, what we claim as new and desire to secure by Letters Patent is:

A new and distinct variety of gladiolus plant, substantially as herein shown and described, characterized by its green color and its good health, good bud count, opening ability after being shipped dry, and modern ruffling.

No references cited.

ABRAHAM G. STONE, *Primary Examiner.*

R. E. BAGWILL, *Assistant Examiner.*